United States Patent
Thimm et al.

(10) Patent No.: US 10,966,865 B2
(45) Date of Patent: Apr. 6, 2021

(54) FEMTOSECOND LASER DOCKING APPARATUS

(71) Applicant: Novartis AG, Basel (CH)

(72) Inventors: Daniel Thimm, Neumarkt in der Oberpfalz (DE); Thomas Deisinger, Cadolzburg (DE)

(73) Assignee: Alcon Inc.

( * ) Notice: Subject to any disclaimer, the term of this patent is extended or adjusted under 35 U.S.C. 154(b) by 198 days.

(21) Appl. No.: 16/039,124

(22) Filed: Jul. 18, 2018

(65) Prior Publication Data

US 2019/0029881 A1    Jan. 31, 2019

Related U.S. Application Data

(60) Provisional application No. 62/537,844, filed on Jul. 27, 2017.

(51) Int. Cl.
*A61F 9/009* (2006.01)
*A61F 9/008* (2006.01)

(52) U.S. Cl.
CPC .......... *A61F 9/009* (2013.01); *A61F 9/00827* (2013.01); *A61F 9/00836* (2013.01); *A61F 9/00825* (2013.01); *A61F 2009/00872* (2013.01)

(58) Field of Classification Search
CPC .................................................. A61F 9/00836
See application file for complete search history.

(56) References Cited

U.S. PATENT DOCUMENTS

| | | | |
|---|---|---|---|
| 2010/0274228 A1* | 10/2010 | Mrochen | A61F 9/009 604/541 |
| 2011/0009851 A1 | 1/2011 | Deisinger et al. | |
| 2011/0190741 A1 | 8/2011 | Kittelmann et al. | |
| 2013/0053837 A1* | 2/2013 | Kandulla | A61F 9/009 606/4 |
| 2013/0102895 A1 | 4/2013 | Gooding et al. | |
| 2013/0338649 A1* | 12/2013 | Hanebuchi | A61F 9/009 606/4 |
| 2015/0190277 A1* | 7/2015 | Gooding | A61F 9/00802 606/6 |
| 2015/0190278 A1* | 7/2015 | Gooding | A61F 9/008 606/4 |
| 2017/0128261 A1 | 5/2017 | Deisinger et al. | |

FOREIGN PATENT DOCUMENTS

EP          3092985 A1    11/2016

\* cited by examiner

*Primary Examiner* — Rex R Holmes
*Assistant Examiner* — Jennifer L Ghand

(57) ABSTRACT

The present disclosure provides a femtosecond laser docking apparatus that includes a suction cone, with an upper frusto-conical portion and lower spherical portion, and a suction ring, with a mechanical stop and at least one contact and sealing surface. The mechanical stop engages the spherical portion of the suction cone to prevent it from being lowered further toward an eye, in a z-direction, beyond the mechanical stop. This disclosure provides a system for femtosecond laser ophthalmic surgery that includes a suction cone, with an upper frusto-conical portion and lower spherical portion, and a suction ring. This disclosure further provides a method for docking a femtosecond laser that includes positioning a suction ring on an eye, lowering a suction cone toward the eye until it engages the mechanical stop of the suction ring, and applying suction to seal the suction cone to the suction ring by a contact and sealing surface.

15 Claims, 6 Drawing Sheets

FEMTOSECOND LASER DOCKING APPARATUS

TECHNICAL FIELD

The present disclosure relates to ophthalmic surgery and surgical equipment, and more specifically, to a femtosecond laser docking apparatus for ophthalmic surgery.

BACKGROUND

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's vision after the surgery.

One type of ophthalmic surgery, refractive eye surgery, is used to correct a variety of vision problems. One common such refractive surgery is known as LASIK (laser-assisted in situ keratomileusis) and is used to correct myopia and hyperopia, astigmatism, or more complex refractive errors. Other ophthalmic surgeries may correct corneal defects or other problems. For instance, phototherapeutic keratectomy (PTK) may be used to remove diseased corneal tissue or corneal irregularities either alone or in combination with LASIK. Another common ophthalmic surgery is the removal of cataracts.

During LASIK, PTK, cataract surgery, and other ophthalmic surgeries, corrective procedures are commonly performed on interior parts of the eye, such as the corneal stroma or the lens, rather than on the eye surface. This practice tends to improve surgical outcomes by allowing the corrective procedure to be targeted to the most effective part of the eye, by keeping the outer, protective parts of the cornea largely intact, and for other reasons.

The interior part of the eye may be accessed in a variety of manners, but frequently access involves cutting a flap in the cornea or otherwise cutting the cornea. Corneal cutting is often performed by a femtosecond laser that creates focused ultrashort pulses, eliminating collateral damage of surrounding tissues associated with slower lasers and complications associated with mechanical cutting instruments, such as blades. Femtosecond lasers can therefore be used to dissect tissue on a microscopic level.

Femtosecond laser ophthalmic surgery typically includes docking, imaging, analysis, and laser treatment.

Generally, during docking, a suction ring is first positioned on a patient's eye and a suction cone is vertically lowered onto the suction ring. The lower portion of the suction cone contacts internal surfaces of the suction ring, and also the patient's eye. By contacting the patient's eye, the suction cone provides pressure to flatten the patient's cornea (known as applanation) and hold it in position for the laser treatment. Docking is a sensitive process, and proper placement of the suction cone is important for successful femtosecond laser ophthalmic surgery. However, correct placement of the suction cone is currently typically guided through visual inspection by the user, relying on experience and perception.

SUMMARY

The present disclosure provides a femtosecond laser docking apparatus comprising a suction cone including an upper frusto-conical portion and a lower spherical portion, and a suction ring including a mechanical stop that extends at least partially around a circumference of a top of the suction ring and that also engages the lower spherical portion of the suction cone to prevent the suction cone from being lowered further toward an eye, in a z-direction, beyond the mechanical stop.

In additional embodiments, which may be combined with one another unless clearly exclusive: the mechanical stop has an upper diameter, and a portion of the suction cone, at a junction of the upper frusto-conical portion and the lower spherical portion, has a junction diameter that is greater than the upper diameter of the of the mechanical stop; the suction cone may be tilted in the x or y-directions while lowered toward the suction ring and be docked without tilt in relation to the suction ring, when the upper stop diameter of the suction cone engages the upper diameter of the mechanical stop; the suction ring further includes at least one contact and sealing surface distinct from the mechanical stop; and the upper frusto-conical portion of the suction cone has a continually decreasing diameter in the z-direction, the diameter also centered around a common axis of the suction cone and the suction ring when the suction cone is positioned on the suction ring and centered in the x-direction and y-direction, wherein the lower spherical portion of the suction cone has a radius ($r_1$) measured from a center point on the common axis to any point on an external surface of the lower spherical portion that engages the contact and sealing surface of the suction ring, wherein a spherical portion of the suction ring has a radius ($r_2$) measured from a center point on the common axis to any contact and sealing surface of the suction ring, and wherein $(r_1)=(r_2)$.

The present disclosure provides a system for femtosecond laser ophthalmic surgery comprising a femtosecond laser, a control device operable to adjust a position of the femtosecond laser, a processor operable to control the control device, a suction cone including an upper frusto-conical portion and a lower spherical portion, the suction cone operable to engage with the femtosecond laser and be lowered toward an eye, in a z-direction, when the position of the femtosecond laser is adjusted, and a suction ring including a mechanical stop that extends at least partially around a circumference of a top of the suction ring and that also engages the spherical portion of the suction cone to prevent the suction cone from being lowered further toward the eye, in the z-direction, beyond the mechanical stop.

In additional embodiments, which may be combined with one another unless clearly exclusive: the mechanical stop has an upper diameter, and a portion of the suction cone, at a junction of the upper frusto-conical portion and the lower spherical portion, has a junction diameter that is greater than the upper diameter of the of the mechanical stop; the suction cone may be tilted in the x or y-directions while lowered toward the suction ring and be docked without tilt in relation to the suction ring, when the upper stop diameter of the suction cone engages the upper diameter of the mechanical stop; the suction ring further includes at least one contact and sealing surface distinct from the mechanical stop; and the upper frusto-conical portion of the suction cone has a continually decreasing diameter in the z-direction, the diameter also centered around a common axis of the suction cone and the suction ring when the suction cone is positioned on the suction ring and centered in the x-direction and y-direction, wherein the lower spherical portion of the suction cone has a radius ($r_1$) measured from a center point on the common axis to any point on an external surface of the lower spherical portion that engages the contact and sealing surface of the suction ring, wherein a spherical portion of the suction ring has a radius ($r_2$) measured from a center point on the common axis to any contact and sealing surface of the suction ring, and wherein ($r_1$)=($r_2$).

The present disclosure further provides a method of docking a femtosecond laser comprising positioning a suction ring on an eye, the suction ring having a mechanical stop that extends at least partially around a circumference of a top of the suction ring, and at least one contact and sealing surface distinct from the mechanical stop, lowering a suction cone having an upper frusto-conical portion and a lower spherical portion, in a z-direction toward the eye such that the mechanical stop of the suction ring engages the spherical portion of the suction cone to prevent the suction cone from being lowered further toward the eye, in the z-direction, and applying suction by at least one vacuum to the suction ring, wherein the suction cone is sealed to the suction ring by contact with the contact and sealing surfaces of the suction ring.

In additional embodiments, which may be combined with one another unless clearly exclusive: the mechanical stop has an upper diameter, and a portion of the suction cone, at a junction of the upper frusto-conical portion and the lower spherical portion, has a junction diameter that is greater than the upper diameter of the of the mechanical stop; the suction cone may be tilted in the x or y-directions while lowered toward the suction ring and be docked without tilt in relation to the suction ring, when the upper stop diameter of the suction cone engages the upper diameter of the mechanical stop; the suction cone is sealed to the suction ring by contact with the contact and sealing surfaces of the suction ring, and not by the mechanical stop; and the upper frusto-conical portion of the suction cone has a continually decreasing diameter in the z-direction, the diameter also centered around a common axis of the suction cone and the suction ring when the suction cone is positioned on the suction ring and centered in the x-direction and y-direction, wherein the lower spherical portion of the suction cone has a radius ($r_1$) measured from a center point on the common axis to any point on an external surface of the lower spherical portion that engages the contact and sealing surface of the suction ring, wherein a spherical portion of the suction ring has a radius ($r_2$) measured from a center point on the common axis to any contact and sealing surface of the suction ring, and wherein ($r_1$)=($r_2$).

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

Figure 1:
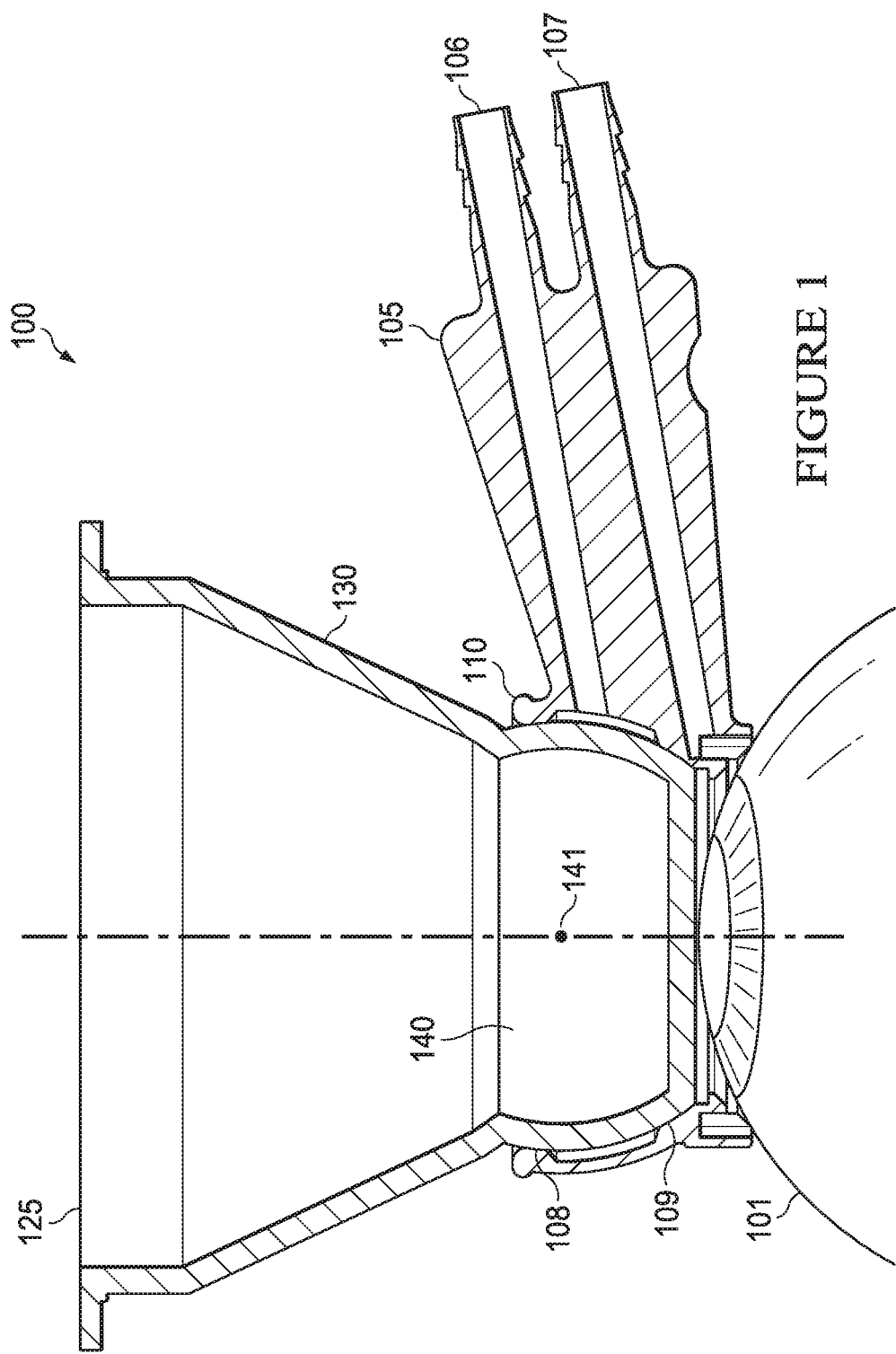
FIG. 1 is a schematic cross-section representation of a femtosecond laser docking apparatus with a suction cone that includes an upper frusto-conical portion and a lower spherical portion.

Referring now to the figures, FIG. 1 is a schematic cross-section of a femtosecond laser docking apparatus 100 with a suction ring 105 and a suction cone 125. Suction ring 105 has contact and sealing surfaces 108 and 109, and mechanical stop 110. Mechanical stop 110 extends at least partially around the circumference of the top of suction ring 105. Mechanical stop 110 may also extend around the entire circumference of the top of suction ring 105. Suction ring 105 includes at least one contact and sealing surface distinct from the mechanical stop 110. Suction ring 105, as shown, is positioned on the eye 101, and is attached to vacuum 106 and vacuum 107. Suction ring 105 also has a spherical portion, which is shown in FIG. 1 on the opposite side of the suction ring from vacuums 106 and 107. This spherical portion of the suction ring receives the lower spherical portion of the suction cone, as it is lowered in the z-direction during docking. The spherical portion of the suction ring and the lower spherical portion of the suction cone both have a positive curvature. As shown, suction ring 105 is properly positioned on the eye, meaning it is centered in the x-direction and the y-direction in relation to a user-defined centering axis, before lowering suction cone 125. The user-defined centering axis may be, for example, the actual center of the eye or the visual axis of the patient.

Suction cone 125 includes an upper frusto-conical portion 130 and a lower spherical portion 140. Upper frusto-conical portion 130 of the suction cone is generally the shape of a cone with the narrow end or tip removed. Upper frusto-conical portion 130 has a continually decreasing diameter, in the z-direction. As used herein, the x and y-directions refer to the plane roughly perpendicular to the apex of the cornea and the z-direction refers to the plane roughly perpendicular to the plane of the x and y-directions. Lower spherical portion 140 of the suction cone is a spherical shape with a positive curvature.

When docking a femtosecond laser, suction ring 105 is positioned on the eye 101 and suction generated by the first vacuum 106 is started. This suction holds the suction ring in place and in contact with the eye. The suction cone 125 is vertically lowered toward the suction ring 105, and when properly positioned on the eye, suction generated by second vacuum 107 may be started to hold suction cone 125 in place and in contact with the eye. As suction cone 125 is vertically lowered, in the z-direction, toward suction ring 105, mechanical stop 110 engages the lower spherical portion 140 of suction cone 125, which prevents the suction cone from being lowered further toward the eye, beyond mechanical stop 110. When lower spherical portion 140 of the suction cone is properly docked to the spherical portion of the suction ring 105, the spherical portions share a common center point, which is also a common point of rotation 141.

Figure 2:
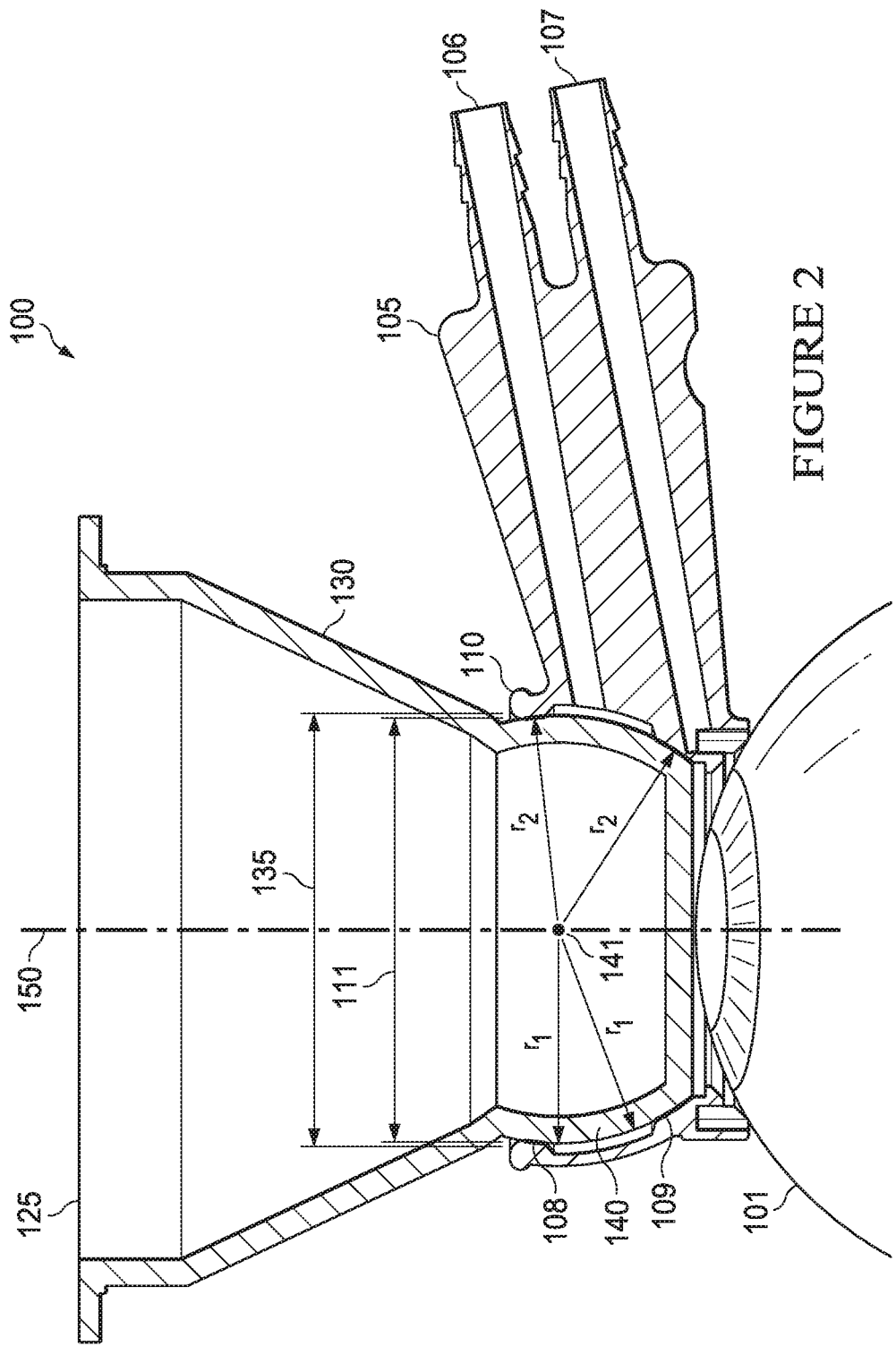
FIG. 2 is a detailed schematic cross-section representation of a femtosecond laser docking apparatus with a suction cone that includes an upper frusto-conical portion and a lower spherical portion.

FIG. 2 is a detailed schematic cross-section representation of femtosecond laser docking apparatus 100 with suction cone 125, which includes an upper frusto-conical portion 130 and a lower spherical portion 140. In FIG. 2, suction ring 105 is properly docked to eye 101 and held in place by first vacuum 106. Suction ring 105 has a mechanical stop 110.

Mechanical stop 110 has an upper diameter 111 that engages suction cone 125 at junction diameter 135. Junction diameter 135 is the diameter at the junction of the upper frusto-conical portion 130 and lower spherical portion 140. When upper diameter 111 engages junction diameter 135, it prevents suction cone 125 from being lowered further toward the eye because the length of junction diameter 135 is greater than the length of upper diameter 111 of the mechanical stop. For example, upper diameter 111 may be 12.0 mm in length and junction diameter 135 may be 12.2 mm in length; thus, when upper diameter 111 engages junction diameter 135, it prevents suction cone 125 from being lowered further toward the eye. In FIG. 2, suction cone 125 has been vertically lowered, in the z-direction toward the suction ring, and the lower spherical portion 140 of the suction cone is properly docked to the suction ring and is held in place by second vacuum 107.

When suction cone 125 is properly docked to the properly positioned suction ring 105, the center of lower spherical portion 140 is centered with the spherical portion of the suction ring 105, in the x and y-directions, around a common axis 150. Along common axis 150, lower spherical portion 140 and the spherical portion of the suction ring 105 share a common point of rotation 141. Suction cone 125 may be tilted in the x-direction or the y-direction while it is lowered in the z-direction toward suction ring 105 and still be docked without tilt in relation to the suction ring, when junction diameter 135 of suction cone 125 engages upper diameter 111 of the mechanical stop.

Lower spherical portion 140 of the suction cone has a radius ($r_1$), measured from point of rotation 141 to any point on its external surface that would engage contact and sealing surface 108 or 109. The spherical portion of the suction ring has radius ($r_2$), measured from point of rotation 141 to any point on the suction ring's contact and sealing surfaces 108 and 109 that would engage lower spherical portion 140. The length of radius ($r_1$) is equal to the length of radius ($r_2$). Because ($r_1$)=($r_2$), when lower spherical portion 140 is properly docked to the spherical portion of suction ring 105, contact and sealing surfaces 108 and 109 allow contact adequate for vacuums 106 and 107 to hold the suction cone and suction ring in place. Each radius ($r_1$) and ($r_2$) may, respectively, be between 2 mm and 25 mm in length, between 5 mm and 20 mm in length, between 6 mm and 15 mm in length, at least 2 mm in length, at least 5 mm in length, at least 6 mm in length, 25 mm or less in length, 20 mm or less in length, or 15 mm or less in length.

Femtosecond laser docking apparatus 100 corrects for difficulty and error related to manually positioning the suction ring during docking. Specifically, the femtosecond laser docking apparatus 100 corrects for tilt of the suction ring on the eye, in the x and y-directions, which may be caused by rotation of the eye. It further prevents the user from having to re-perform applanation and docking in situations where it is discovered afterward that the suction ring is tilted and vacuum suction is deficient. When mechanical stop 110 engages junction diameter 135, femtosecond laser docking apparatus 100 prevents suction cone 125 from inadvertently contacting the eye even if the suction cone is tilted in the x or y-directions, while being lowered in the z-direction. Femtosecond laser docking apparatus 100 allows the user to perform the docking procedure faster and with fewer complications, which decreases stress on the patient caused by suction on the eye and having to remain still throughout docking and treatment. Femtosecond laser docking apparatus 100 further decreases the potential for damage to blood vessels of the eye and other internal structures which may be caused by re-performing the docking procedure and prolonged periods of suction.

Figure 3:
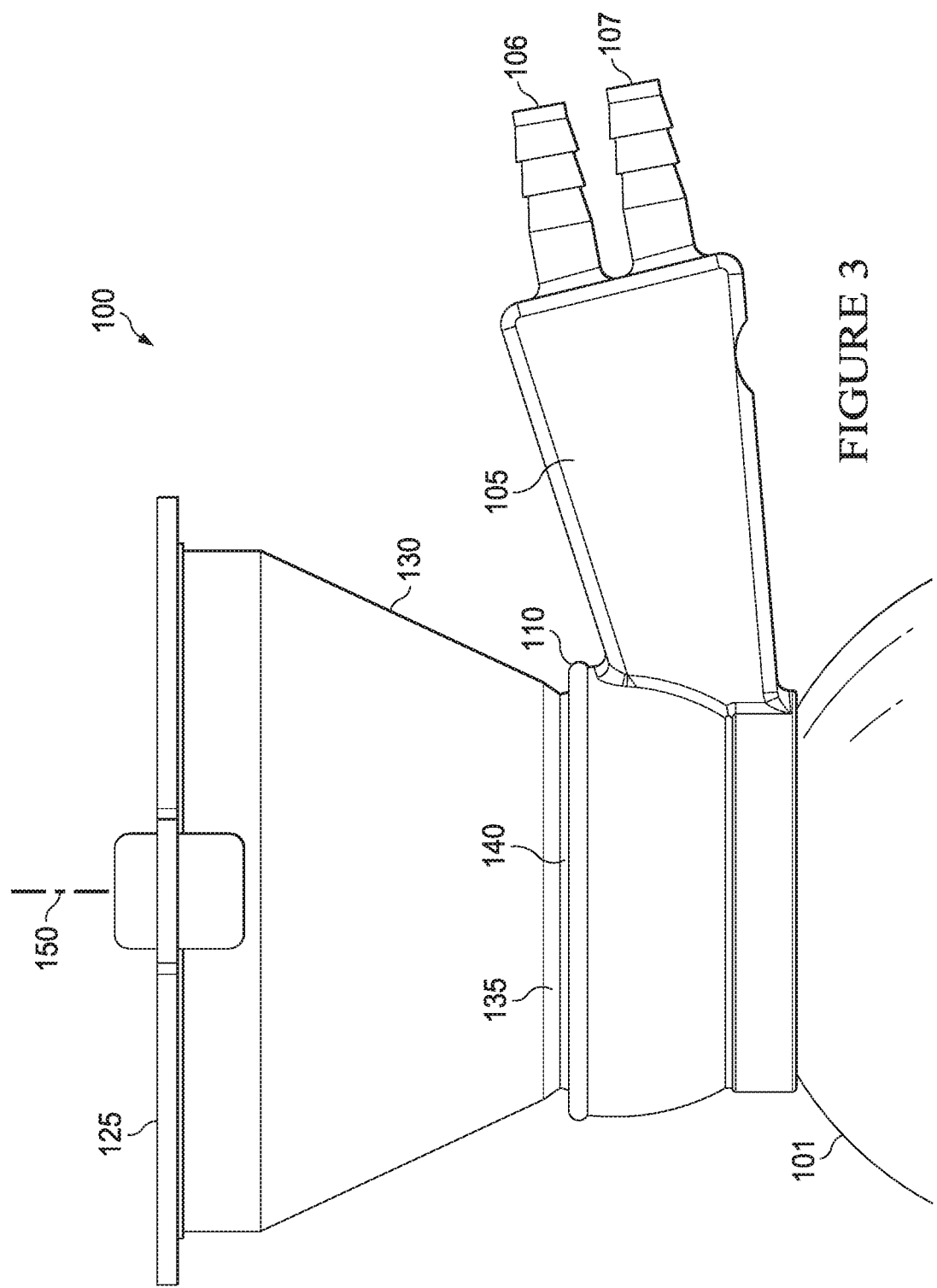
FIG. 3 is a schematic 3-dimensional ("3D") representation of an femtosecond laser docking apparatus with a suction cone that includes an upper frusto-conical portion and a lower spherical portion.

FIG. 3 is a schematic 3D representation of femtosecond laser docking apparatus 100, which includes suction ring 105 and suction cone 125. Suction cone 125 includes upper frusto-conical portion 130, lower spherical portion 140, and junction diameter 135. As shown, suction ring 105 is properly positioned on the eye, meaning it is centered in the x-direction and the y-direction in relation to a user-defined centering axis, before lowering suction cone 125. In FIG. 3, suction cone 125 has been lowered in the z-direction until junction diameter 135 has engaged mechanical stop 110. Suction cone 125 is properly docked to suction ring 105 and they are held in place and in contact with the eye 101 by vacuums 106 and 107. Because suction cone 125 is properly docked to suction ring 105, which is properly positioned on the eye in the x and y-directions, both are centered in the x and y-directions around common axis 150.

Figure 4:
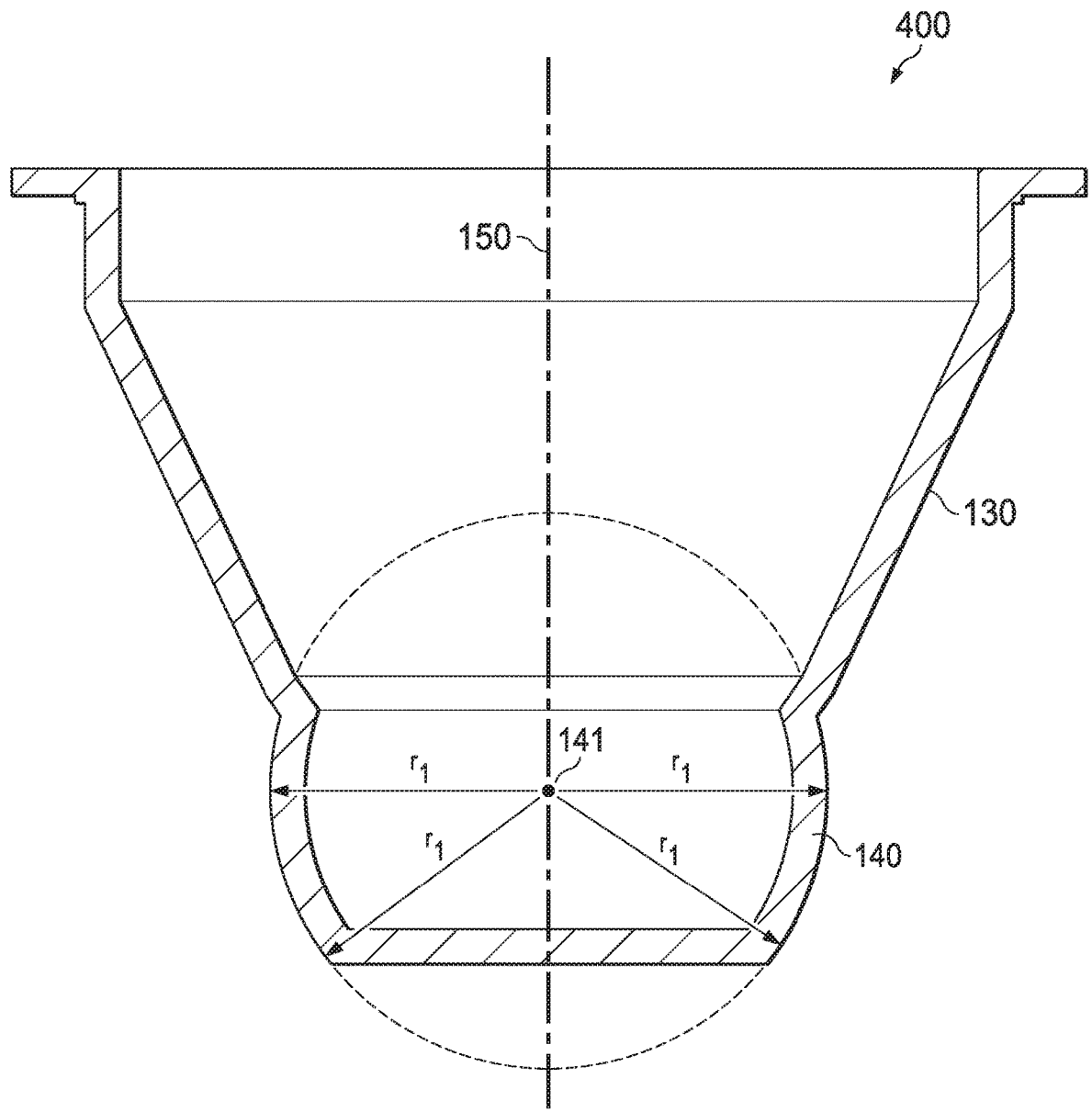
FIG. 4 is a schematic representation of the spherical shape of the lower spherical portion of the suction cone.

FIG. 4 is a schematic representation 400 of the spherical shape of the lower spherical portion 140 of the suction cone. Lower spherical portion 140 has a radius ($r_1$), measured from its center point, which as shown is point of rotation 141, to any point on its external surface that would engage a contact and sealing surface of the suction ring. The length of radius ($r_1$), of lower spherical portion 140, is equal to the length of a radius ($r_2$) of the spherical portion of the suction ring. Thus, when the suction cone and suction ring are properly docked together, those spherical portions essentially form concentric spherical shapes with a common point of rotation 141. Each radius ($r_1$) and ($r_2$) may, respectively, be between 2 mm and 25 mm in length, between 5 mm and 20 mm in length, between 6 mm and 15 mm in length, at least 2 mm in length, at least 5 mm in length, at least 6 mm in length, 25 mm or less in length, 20 mm or less in length, or 15 mm or less in length.

Figure 5:
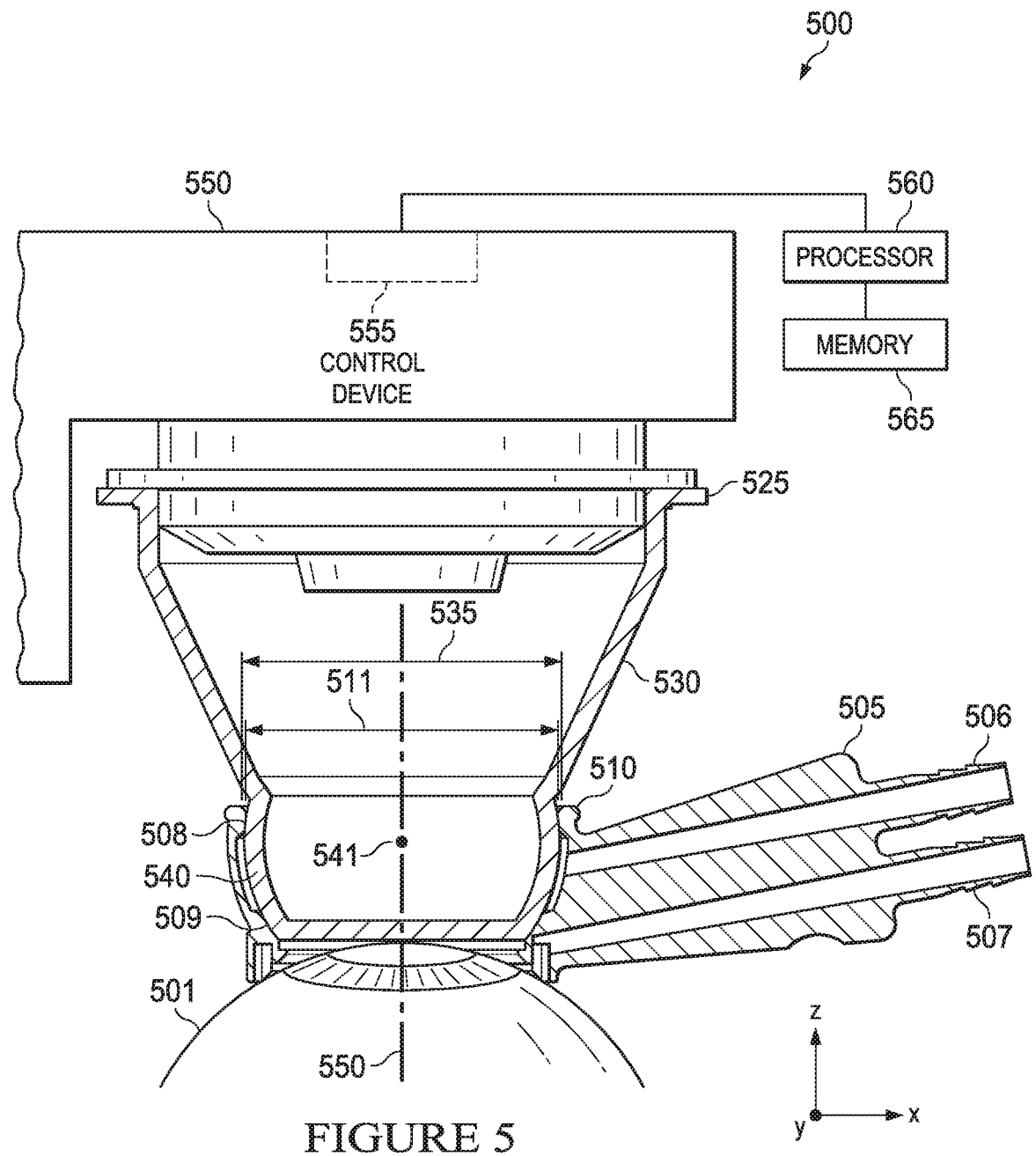
FIG. 5 is a schematic diagram of a system for femtosecond laser ophthalmic surgery.

FIG. 5 is a schematic diagram of a system 500 for femtosecond laser ophthalmic surgery. System 500 includes a femtosecond laser 550, which has a control device 555 to adjust a position of the femtosecond laser, processor 560 to control the control device, memory 565, suction ring 505 and a suction cone 525. Control device 555 may adjust a position of femtosecond laser 550 in any of the x, y, or z-directions. As described in FIG. 1 and FIG. 2, suction cone 525 has an upper frusto-conical portion 530 and a lower spherical portion 540. Suction cone 525 may engage with the femtosecond laser 550 and be lowered toward an eye, in a z-direction, when the position of the femtosecond laser is adjusted via control device 555. The upper frusto-conical portion of the suction cone has a continually decreasing diameter, in the z-direction. Suction cone 525 has a junction diameter 535, which is the diameter at the junction of the upper frusto-conical portion 530 and lower spherical portion 540.

Also as described in FIG. 1 and FIG. 2, the suction ring 505 has contact and sealing surfaces 508 and 509, and mechanical stop 510. Mechanical stop 510 extends at least partially around the circumference of the top of suction ring 505. Mechanical stop 510 may also extend around the entire circumference of the top of suction ring 505. Suction ring 505 includes at least one contact and sealing surface distinct from the mechanical stop 510. Suction ring 505, as shown, is positioned on the eye 501, and is attached to vacuum 506 and vacuum 507. In FIG. 5, suction ring 505 is properly positioned on the eye, meaning it is centered in the x-direction and the y-direction in relation to a user-defined centering axis, before lowering suction cone 525. The user-defined centering axis may be, for example, the actual center of the eye or the visual axis of the patient.

To dock femtosecond laser 550 on the eye 501, suction ring 505 is positioned on the eye and suction generated by the first vacuum 506 is started. This suction holds the suction ring in place and in contact with the eye. The suction cone 525 is vertically lowered toward the suction ring 505, and when properly positioned, suction generated by second vacuum 507 may be started to hold suction cone 525 in place and in contact with the eye.

Suction cone 525 is vertically lowered, in the z-direction, toward suction ring 505, until mechanical stop 510 engages spherical portion 540 of the suction cone, preventing the suction cone from being lowered further toward the eye beyond mechanical stop 510. Mechanical stop 510 has an upper diameter 511 that engages junction diameter 535, of suction cone 525. When mechanical stop 510 engages junction diameter 535, it prevents suction cone 525 from being lowered further toward the eye because the length of junction diameter 535 is greater than the length of upper diameter 511 of the mechanical stop.

When the suction cone 525 is properly docked to the properly positioned suction ring 505, the suction cone and suction ring are centered in the x and y-directions, around a common axis 550, and have a common point of rotation 541. Suction cone 525 may be tilted in the x-direction or the y-direction while it is lowered toward suction ring 505 and still be docked without tilt in relation to the suction ring, when junction diameter 535 of the suction cone engages upper diameter 511 of the mechanical stop.

System 500 for femtosecond laser ophthalmic surgery corrects for difficulty and error related to manually positioning the suction ring during docking. Specifically, system 500 corrects for tilt of the suction ring on the eye, in the x and y-directions, which may be caused by rotation of the eye. It further prevents the user from having to re-perform applanation and docking in situations where it is discovered afterward that the suction ring is tilted and vacuum suction is deficient. When mechanical stop 511 engages junction diameter 535, system 500 prevents suction cone 525 from inadvertently contacting the eye even if the suction cone is tilted in the x or y-directions, while being lowered in the z-direction. System 500 allows the user to perform the docking procedure faster and with fewer complications, which decreases stress on the patient caused by suction on the eye and having to remain still throughout docking and treatment. System 500 further decreases the potential for damage to blood vessels of the eye and other internal structures which may be caused by re-performing the docking procedure and prolonged periods of suction.

Processor 560 may comprise, for example a microprocessor, microcontroller, digital signal processor (DSP), application specific integrated circuit (ASIC), or any other digital or analog circuitry configured to interpret and/or execute program instructions and/or process data. In some embodiments, processor 560 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 6:
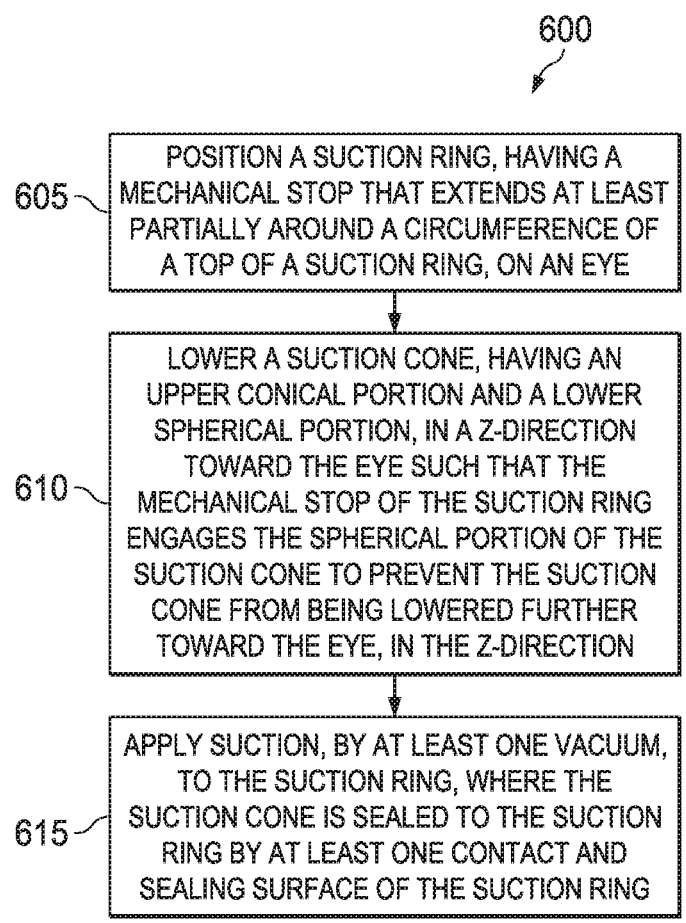
FIG. 6 is a flowchart of a method for docking a femtosecond laser.

FIG. 6 is a flowchart of a method 600 for docking a femtosecond laser. At step 605, a suction ring is positioned on an eye, the suction ring having a mechanical stop that extends at least partially around a circumference of a top of the suction ring. The mechanical stop of the suction ring has an upper diameter. The suction ring may further include at least one contact and sealing surface distinct from the mechanical stop.

At step 610, the suction cone, having an upper frusto-conical portion and a lower spherical portion, is lowered in a z-direction toward the eye until the mechanical stop of the suction ring engages the spherical portion of the suction cone, preventing the suction cone from being lowered further toward the eye, in the z-direction. The upper frusto-conical portion of the suction cone has a continually decreasing diameter, in the z-direction. A portion of the suction cone, at a junction of the upper frusto-conical portion and the lower spherical portion, has a junction diameter that is greater than the upper diameter of the mechanical stop. Because the length of the junction diameter of the suction cone is greater than the length of the upper diameter of the mechanical stop, the mechanical stop prevents the suction cone from being lowered past the mechanical stop in the z-direction. When lowering the suction cone in the z-direction, toward the eye, the suction cone may contact at least one contact and sealing surface of the suction ring. Contact between the suction cone and the contact and sealing surface(s) allows for sufficient vacuum pressure to hold the suction cone and suction ring in position and in contact with the eye.

The lower spherical portion of the suction cone has a radius ($r_1$), measured from its center point to any point on its external surface that would engage a contact and sealing surface of the suction ring. The length of radius ($r_1$) is equal to the length of a radius ($r_2$) of the spherical portion of the suction ring, so when the suction cone is properly docked to the suction ring, those spherical portions essentially form concentric spherical shapes with a common point of rotation.

At step 615, suction is applied, by at least one vacuum, to the suction ring, where the suction cone is sealed to the suction ring by the contact and sealing surface(s) of the suction ring. The suction cone is sealed to the suction ring by the contact and sealing surfaces of the suction ring, and not by the mechanical stop.

Method 600 allows the suction cone to be tilted in the x or y-directions while lowered, at step 610, toward the suction ring and be docked without tilt in relation to the suction ring, when at least the upper stop diameter of the suction cone engages the upper diameter of the mechanical stop. Method 600 corrects for difficulty and error related to manually positioning the suction ring during docking, in particular with in relation to tilt of the suction ring on the eye, which may be caused by rotation of the eye. Method 600 further prevents the user from having to re-perform applanation and docking in situations where it is discovered afterward that the suction ring is tilted and vacuum suction is deficient. This allows the user to perform the docking procedure faster and with fewer complications, which decreases stress on the patient caused by suction on the eye and having to remain still throughout docking and treatment. Such methods decrease the potential for damage to blood vessels of the eye and other internal structures which may be caused by re-performing the docking procedure and prolonged periods of suction.

Method 600 may be implemented using the femtosecond laser ophthalmic surgery system of FIG. 5, or any other suitable system. The preferred initialization point for such methods and the order of their steps may depend on the implementation chosen. In some embodiments, some steps may be optionally omitted, repeated, or combined. In some embodiments, some steps of such methods may be executed in parallel with other steps. In certain embodiments, the methods may be implemented partially or fully in software embodied in computer-readable media.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such wires, optical fibers, and other electromagnetic and/or optical carriers; and/or any combination of the foregoing.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A femtosecond laser docking apparatus comprising:
   a suction cone including an upper frusto-conical portion and a lower spherical portion; and
   a suction ring including a spherical portion and a mechanical stop that extends at least partially around a circumference of a top of the suction ring, the mechanical stop having an upper diameter; the suction ring engaging the lower spherical portion of the suction cone; the mechanical stop preventing the suction cone from being lowered further toward an eye, in a z-direction, beyond the mechanical stop;
   wherein the spherical portion of the suction ring engages the lower spherical portion of the suction cone such that the lower spherical portion of the suction cone swivels with respect to the suction ring until the suction cone engages the mechanical stop.

2. The apparatus of claim 1, wherein a portion of the suction cone, at a junction of the upper frusto-conical portion and the lower spherical portion, has a junction diameter that is greater than the upper diameter of the of the mechanical stop.

3. The apparatus of claim 2, wherein the suction cone may be tilted in the x or y-directions while lowered toward the suction ring and be docked without tilt in relation to the suction ring, when the junction diameter of the suction cone engages the upper diameter of the mechanical stop.

4. The apparatus of claim 1, wherein the suction ring further includes at least one contact and sealing surface distinct from the mechanical stop.

5. The apparatus of claim 4, wherein the upper frusto-conical portion of the suction cone has a continually decreasing diameter in the z-direction, the diameter also centered around a common axis of the suction cone and the suction ring when the suction cone is positioned on the suction ring and centered in the x-direction and y-direction,
   wherein the lower spherical portion of the suction cone has a radius ($r_1$) measured from a center point on the common axis to any point on an external surface of the lower spherical portion that engages the contact and sealing surface of the suction ring,
   wherein the spherical portion of the suction ring has a radius ($r_2$) measured from a center point on the common axis to any contact and sealing surface of the suction ring, and
   wherein ($r_1$)=($r_2$).

6. A system for femtosecond laser ophthalmic surgery comprising:
   a femtosecond laser;
   a control device operable to adjust a position of the femtosecond laser;
   a processor operable to control the control device;
   a suction cone including an upper frusto-conical portion and a lower spherical portion, the suction cone operable to engage with the femtosecond laser and be lowered toward an eye, in a z-direction, when the position of the femtosecond laser is adjusted; and
   a suction ring including a spherical portion and a mechanical stop that extends at least partially around a circumference of a top of the suction ring, the mechanical stop having an upper diameter; the suction ring engaging the lower spherical portion of the suction cone; the mechanical stop preventing the suction cone from being lowered further toward an eye, in a z-direction, beyond the mechanical stop;
   wherein the spherical portion of the suction ring engages the lower spherical portion of the suction cone such that the lower spherical portion of the suction cone swivels with respect to the suction ring until the suction cone engages the mechanical stop.

7. The system of claim 6, wherein a portion of the suction cone, at a junction of the upper frusto-conical portion and the lower spherical portion, has a junction diameter that is greater than the upper diameter of the of the mechanical stop.

8. The apparatus of claim 7, wherein the suction cone may be tilted in the x or y-directions while lowered toward the suction ring and be docked without tilt in relation to the suction ring, when the upper stop diameter of the suction cone engages the upper diameter of the mechanical stop.

9. The system of claim 6, wherein the suction ring further includes at least one contact and sealing surface distinct from the mechanical stop.

10. The system of claim 9, wherein the upper frusto-conical portion of the suction cone has a continually decreasing diameter in the z-direction, the diameter also centered around a common axis of the suction cone and the suction ring when the suction cone is positioned on the suction ring and centered in the x-direction and y-direction,
    wherein the lower spherical portion of the suction cone has a radius ($r_1$) measured from a center point on the common axis to any point on an external surface of the lower spherical portion that engages the contact and sealing surface of the suction ring, wherein the spherical portion of the suction ring has a radius ($r_2$) measured from a center point on the common axis to any contact and sealing surface of the suction ring, and wherein ($r_1$)=($r_2$).

11. A method of docking a femtosecond laser comprising:

positioning a suction ring, having a spherical portion and a mechanical stop that extends at least partially around a circumference of a top of the suction ring, the mechanical stop having an upper diameter; and at least one contact and sealing surface distinct from the mechanical stop, on an eye;

lowering a suction cone, having an upper frusto-conical portion and a lower spherical portion, in a z-direction toward the eye such that the mechanical stop of the suction ring engages the lower spherical portion of the suction cone; the mechanical stop preventing the suction cone from being lowered further toward the eye, in the z-direction; and applying suction by at least one vacuum to the suction ring, wherein the suction cone is sealed to the suction ring by contact with the contact and sealing surfaces of the suction ring wherein the spherical portion of the suction ring engages the lower spherical portion of the suction cone such that the lower spherical portion of the suction cone swivels with respect to the suction ring until the suction cone engages the mechanical stop.

12. The method of claim 11, wherein a portion of the suction cone, at a junction of the upper frusto-conical portion and the lower spherical portion, has a junction diameter that is greater than the upper diameter of the of the mechanical stop.

13. The method of claim 12, wherein the suction cone may be tilted in the x or y-directions while lowered toward the suction ring and be docked without tilt in relation to the suction ring, when the upper stop diameter of the suction cone engages the upper diameter of the mechanical stop.

14. The method of claim 11, wherein the suction cone is sealed to the suction ring by contact with the contact and sealing surfaces of the suction ring, and not by the mechanical stop.

15. The method of claim 14, wherein the upper frusto-conical portion of the suction cone has a continually decreasing diameter in the z-direction, the diameter also centered around a common axis of the suction cone and the suction ring when the suction cone is positioned on the suction ring and centered in the x-direction and y-direction, wherein the lower spherical portion of the suction cone has a radius ($r_1$) measured from a center point on the common axis to any point on an external surface of the lower spherical portion that engages the contact and sealing surface of the suction ring, wherein the spherical portion of the suction ring has a radius ($r_2$) measured from a center point on the common axis to any contact and sealing surface of the suction ring, and wherein ($r_1$)=($r_2$).

* * * * *